(12) United States Patent
Ober et al.

(10) Patent No.: US 8,641,816 B2
(45) Date of Patent: Feb. 4, 2014

(54) VINYL ETHER COMPOUNDS AND METHODS OF THEIR PREPARATION AND USE

(75) Inventors: Matthias S. Ober, Midland, MI (US); Edward D. Daugs, Midland, MI (US); Wanglin Yu, Midland, MI (US); Cynthia L. Rand, Sanford, MI (US)

(73) Assignee: Dow Global Technologies LLC, Midland, MI (US)

( * ) Notice: Subject to any disclaimer, the term of this patent is extended or adjusted under 35 U.S.C. 154(b) by 444 days.

(21) Appl. No.: 12/909,370

(22) Filed: Oct. 21, 2010

(65) Prior Publication Data

US 2011/0105507 A1    May 5, 2011

Related U.S. Application Data

(60) Provisional application No. 61/257,625, filed on Nov. 3, 2009.

(51) Int. Cl.

| | |
|---|---|
| C07C 41/24 | (2006.01) |
| C07C 43/16 | (2006.01) |
| C07C 43/17 | (2006.01) |
| C07D 295/088 | (2006.01) |
| A61K 31/08 | (2006.01) |
| A61K 31/5375 | (2006.01) |
| C09D 7/12 | (2006.01) |
| C09D 11/02 | (2006.01) |

(52) U.S. Cl.
USPC ............ 106/287.2; 514/239.2; 514/715; 514/716; 514/719; 514/722; 514/723; 106/287.23; 106/31.13; 549/177; 568/589; 568/633; 568/665; 568/673; 568/686; 568/687; 568/692

(58) Field of Classification Search
None
See application file for complete search history.

(56) References Cited

U.S. PATENT DOCUMENTS

| | | | |
|---|---|---|---|
| 3,590,009 A | 6/1971 | Gurgiolo et al. | |
| 3,799,947 A | 3/1974 | Gurgiolo et al. | |
| 2009/0281359 A1 | 11/2009 | Daugs et al. | |

FOREIGN PATENT DOCUMENTS

| | | |
|---|---|---|
| CA | 2251764 | 10/1997 |
| DE | 1919238 | 12/1970 |
| FR | 2040873 | 1/1971 |
| JP | 52008886 | 3/1977 |

OTHER PUBLICATIONS

Chaurasia et al., caplus an 2008:238519.*
Taskinen et al., caplus an 1975:496123.*
Taskinen, caplus an 1977:71604, 1977.*

Berger et al., "Polymerization of p-cresyl glycidyl ether induced by benzyldimethylamine", European Polymer Journal, 1985, vol. 21 No. 5, pp. 435-444.
Brouwer et al., "A new synthesis of 4-OR*-3-penten-1-ynes (C5-fragment) as a tool for the preparation of vitamin A." Recueil, Journal of the Royal Netherlands Chemical Society, 1979, vol. 98 No. 5, pp. 316-320.
Denmark et al., "Carbanion-accelerated Claisen rearrangements. 6. Preparative and stereochemical studies with sulfonyl-stabilized anions", Journal of the American Chemical Society, 1989, vol. 111 No. 24, pp. 8878-8891.
Denmark et al., "Studies on the addition of allyl oxides to sulfonylallenes. Preparation of highly substituted allyl vinyl ethers for carbanionic Claisen rearrangements", Journal of Organic Chemistry, 1987, vol. 52 No. 18, pp. 4031-4042.
Gu et al., "2-Chloro-1-(chloromethyl)ethyl Methoxymethyl Ether as a Reagent for Acetonylation of Alcohols and Phenol", Journal of Organic Chemistry, 1986, vol. 51, pp. 5425-5427.
Ikeda et al., "One-step synthesis of oxodimethylenemethane-Transition Metal Complexes and Palladium-Catalyzed Cycloaddition Reaction", Journal of Organic Chemistry, 1996, vol. 61 No. 15, pp. 4971-4974.
Janicki et al., "A Facile, General Approach to the Synthesis of Electrophilic Acetone Equivalents", Journal of Organic Chemistry, 1998, vol. 63 No. 11, pp. 3694-3700.
Maezaki et al., "A novel asymmetric desymmetrisation of meso-cyclopentane-1,2-diol via diastereoselective β-elimination of chrial α-arylsulfinyl acetals", Journal of the Chemical Society, Chemical Communications, 1994, vol. 11, pp. 1345-1346.
Maezaki et al., "Novel asymmetric desymmetrization of meso-1,2-diols via diastereoselective β-elimination of chiral α-arylsulfinyl acetals", Tetrahedron, 1996, vol. 52 No. 19, pp. 6527-6546.
Matejka et al., "Model reactions of amine curing of glycidylamine epoxy resins: homopolymerization of N-methylglycidylaniline", Journal of Polymer Science. Part A: Polymer Chemistry, 1992, vol. 30 No. 10, pp. 2109-2120.
Moazzam et al., "Addition of ethyl alcohol to triethylpropargylammonium bromide", Iranian Journal of Chemistry & Chemical Engineering, 1990, vol. 13, pp. 53-56.
Criegee et al., Database Reaxys, 1956, vol. 89, Abstract.
Janicki et al., "A Facile, General Approach to the Synthesis of Electrophilic Acetone Equivalents", Journal of Organic Chemistry, 1998, vol. 63, pp. 3694-3700, American Chemical Society.
Taskinen et al., "Thermodynamics of Vinyl Ethers—XV", Tetrahedron, 1976, vol. 32, pp. 593-595, Pergamon Press.
Taskinen, "Thermodynamics of Vinyl Ethers—XVII", Tetrahedron, 1976, vol. 32, pp. 2327-2329, Pergamon Press.
International Search Report and Written Opinion for PCT/US2010/053535 dated Apr. 20, 2011.

* cited by examiner

*Primary Examiner* — Sun Jae Loewe

(57) ABSTRACT

Provided are new functionalized surfactants and methods of their preparation and use. The surfactants are compounds of formula I:

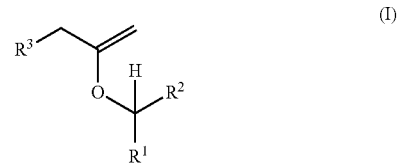

wherein $R^1$, $R^2$, and $R^3$ are as defined herein.

8 Claims, No Drawings

VINYL ETHER COMPOUNDS AND METHODS OF THEIR PREPARATION AND USE

This application claims priority to U.S. provisional application Ser. No. 61/257,625, filed Nov. 3, 2009, which is incorporated herein by reference in its entirety.

FIELD OF THE INVENTION

The invention relates to new vinyl ether compounds, and compositions and methods of preparation and use thereof.

BACKGROUND OF THE INVENTION

Vinyl ethers are an important class of materials that find wide spread use in a variety of applications. For instance, they can be used in radiation curable compositions, as monomeric building blocks in polymers and copolymers, in coatings and adhesives, as surfactants, as reactive diluents, and in printing inks.

Vinyl ethers are generally produced industrially by the Reppe process. The process involves an addition reaction between acetylene and an alcohol in the presence of a catalyst. The process, however, is disadvantageous because the acetylene is difficult to handle and may give rise to decomposition and explosions at a high pressure. Thus, complex controls are required for handling of the acetylene. In addition, while some structural diversity of products can be provided by varying the structure of the alcohol, suitable acetylene derivatives are not widely available, thus limiting the variety of compounds that can be prepared.

It would be a significant advance in the art to provide new, structurally diverse, vinyl ether compounds, and processes for making them.

BRIEF SUMMARY OF THE INVENTION

In one aspect, the invention provides vinyl ether compounds. The compounds are of the formula I:

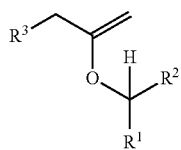

(I)

wherein $R^1$ $R^2$, and $R^3$ are as defined below.

In another aspect, the invention provides compositions comprising two or more compounds of formula I.

In a further aspect, the invention provides formulations containing one or more compounds of formula I.

In a still further aspect, the invention provides a process for making compounds of formula I and compositions thereof.

DETAILED DESCRIPTION OF THE INVENTION

As noted above, the invention provides vinyl ether compounds. The compounds may be substituted with a wide variety of further functional groups, many of which were not previously readily accessible by prior art methods. Because of their structural diversity, the vinyl ethers can be used in a multitude of applications, including, for instance, as surfactants, polymerizable surfactants, co-monomers for UV cure applications, as reactive diluents, and as co-monomers for high $T_g$/low $\epsilon_r$ polymers.

The processes described below for preparing the vinyl ethers of the invention may result in the formation of mixtures of vinyl ether compounds. Although the individual compounds may be isolated from the mixture, this step is not necessary, and indeed it is sometimes preferred that the vinyl ethers be used in the form of the mixture. Thus, compositions of vinyl ether mixtures are contemplated and are within the scope of the invention.

The vinyl ethers of the invention are compounds of formula I:

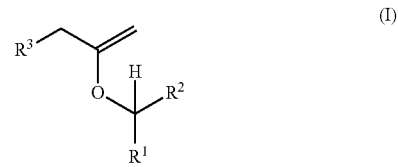

(I)

wherein $R^1$ is $C_1$-$C_{12}$ alkyl or $C_5$-$C_8$ cycloalkyl;
$R^2$ is $C_1$-$C_{23}$ alkyl or $C_5$-$C_8$ cycloalkyl;
or $R^1$ and $R^2$, together with the carbon to which they are attached, form $C_5$-$C_8$ cycloalkyl;
$R^3$ is $SO_3^-M^+$, a tertiary amine, a quaternary ammonium, a tertiary phosphine, a quaternary phosphonium, alkenyloxy, alkoxy, poly(alkoxy), alkynyloxy, aryloxy, cycloalkenyloxy, cycloalkoxy, halo, haloalkyloxy, aminoalkyloxy, (trialkylammonio)alkyloxy, hydroxyalkyl-amino, aryloxy-alkoxy, heterocycloalkyl, or thioether;
$M^+$ is $H^+$ or a monovalent or divalent cation,
wherein the total number of carbon atoms in $R^1$, $R^2$ and the carbon to which they are attached is 4 to 22;

In some embodiments, the vinyl ethers are compounds of formula I-1, which are compounds of formula I in which $R^1$ is methyl.

In some embodiments, the vinyl ethers are compounds of formula I-2, which are compounds of formula I or I-1 in which $R^2$ is a $C_1$-$C_{19}$ alkyl. In further embodiments, $R^2$ is $C_1$-$C_{15}$ alkyl.

In some embodiments, the vinyl ethers are compounds of formula I-3, which are compounds of formula I or I-1 in which $R^2$ is $C_5$-$C_8$ cycloalkyl.

In some embodiments, the vinyl ethers are compounds of formula I-4, which are compounds of formula I in which $R^1$ is methyl and $R^2$ is $C_1$-$C_{15}$ alkyl. In further embodiments, $R^2$ is linear alkyl. In still further embodiments the total number of carbon atoms in $R^1$, $R^2$ and the carbon to which they are attached, is 4-20, alternatively 4-18, alternatively 4-16, or alternatively 4-14. In yet further embodiments the total number of carbon atoms in $R^1$, $R^2$ and the carbon to which they are attached, is alternatively 5-22, alternatively 5-20, alternatively 5-18, alternatively 5-16, or alternatively 5-14. In still yet further embodiments the total number of carbon atoms in $R^1$, $R^2$ and the carbon to which they are attached, is 6-22, alternatively 6-20, alternatively 6-18, alternatively 6-16, or alternatively 6-14.

In some embodiments, the vinyl ethers are compounds of formula I-5, which are compounds of formula I or I-1 in which $R^1$ and $R^2$, together with the carbon to which they are attached, form $C_5$-$C_8$ cycloalkyl. In further embodiments, $R^1$ and $R^2$, together with the carbon to which they are attached, form $C_5$-$C_7$ cycloalkyl, and in still further embodiments they form cyclohexyl or norbornyl.

In some embodiments, the vinyl ethers are compounds of formula I-6, which are compounds of formula I, I-1, I-2, I-3, I-4, or I-5 in which $R^3$ is $SO_3^-M^+$, a tertiary amine, a tertiary phosphine, a quaternary ammonium, a quaternary phosphonium, alkenyloxy, alkoxy, poly(alkoxy) (including polyethers up to a molecular weight of 1000), aryloxy, halo, an aminoalkyloxy, (trialkylammonio)alkyloxy, morpholino, or thioether. In some embodiments, when $R^3$ is thioether, the total number of carbon atoms in $R^1$, $R^2$ and the carbon to which they are attached is 7 to 22, or alternatively 7 to 20.

In some embodiments, the vinyl ethers are compounds of formula I-7, which are compounds of formula I, I-1, I-2, I-3, I-4, I-5, or I-6 in which $R^3$ is a tertiary amine, a quaternary ammonium, alkenyloxy, alkoxy, poly(alkoxy), aryloxy, hydroxyalkyl-amino, aryloxy-alkoxy, heterocycloalkyl, or halo.

Preferred poly(alkoxy) moieties under formula I-7 are groups having the formula $R^4$—$(OCHR^5CHR^6)_y$—O—, where $R^4$ is $C_1$-$C_4$ alkyl (preferably methyl), $R^5$ and $R^6$ are independently H or $C_1$-$C_3$ alkyl (each is preferably H), and y is the number of repeating units and is at least 1. Preferably, the molecular weight of the poly(alkoxy) is up to about 10000, more preferably up to about 1000, further preferably up to about 500. When $R^3$ is $SO_3^-M^+$, in some embodiments it is preferred that $M^+$ be $H^+$, $Na^+$, $K^+$, ammonium or alkylated ammonium. In still further embodiments, $Na^+$ preferred.

In some embodiments, the vinyl ethers of the invention are compounds as shown in Table 1:

TABLE 1

| Name | Structure |
|---|---|
| Triethyleneglycol methyl 2-dodecyloxyallyl ether | $H_3C$—$(OH_2CH_2C)_3$—O... |
| 2-(3-(2-phenoxyethoxy)-prop-1-en-2-yloxy)bicyclo-[2.2.1]heptane | 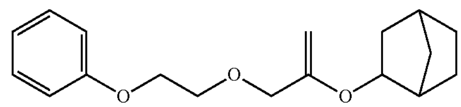 [SMILES: C=C(COCCOc1ccccc1)OC1CC2CCC1C2] |
| (3-(allyloxy)prop-1-en-2-yloxy)hexane and isomers encompassed by formula I | ...O—$C_6H_{13}$ |
| (3-chloroprop-1-en-2-yloxy)hexane and isomers encompassed by formula I. | Cl...O...$C_6H_{13}$ |
| Polyethyleneglycol methyl 2-dodecyloxyallyl ether | ...O—$(CH_2CH_2O)_{12}$—$CH_3$ |
| 2-(3-(allyloxy)prop-1-en-2-yloxy)bicyclo[2.2.1]heptane | 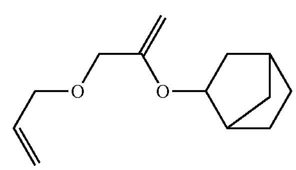 |
| (3-(allyloxy)prop-1-en-2-yloxy)dodecane and isomers encompassed by formula I. | O...$C_{12}H_{25}$ |
| 2-(2-(hexanyloxy)allyloxy)-N,N-dimethylethanamine and isomers encompassed by formula I. | $Me_2N$...O...$C_6H_{13}$ |
| 2-(2-(dodecanyloxy)-allyloxy)-N,N-dimethylethanamine and isomers encompassed by formula I. | $Me_2N$...O...$C_{12}H_{25}$ |

TABLE 1-continued

| Name | Structure |
|---|---|
| N,N-dimethyl-2-(2-methyldodecanyloxy)prop-2-en-1-amine and isomers encompassed by formula I. | Me$_2$N–CH$_2$–C(=CH$_2$)–O–C$_{12}$H$_{25}$ |
| 2-(2-(dodecanyloxy)-allyloxy)-N,N,N-trimethylethanaminium bromide and isomers encompassed by formula I. | Me$_3$N$^+$–CH$_2$CH$_2$–O–CH$_2$–C(=CH$_2$)–O–C$_{12}$H$_{25}$, Br$^-$ |
| 2-(dodecanyloxy)-N,N,N-trimethylprop-2-en-1-aminium bromide and isomers encompassed by formula I. | Me$_3$N$^+$–CH$_2$–C(=CH$_2$)–O–C$_{12}$H$_{25}$, Br$^-$ |
| (3-chloroprop-1-en-2-yloxy)bicyclo[2.2.1]heptane | Cl–CH$_2$–C(=CH$_2$)–O–bicyclo[2.2.1]heptyl |
| Sodium 2-(hexyloxy)prop-2-ene-1-sulfonate and isomers encompassed by formula I. | NaSO$_3$–CH$_2$–C(=CH$_2$)–O–C$_6$H$_{13}$ |
| (3-chloroprop-1-en-2-yloxy)octane and isomers encompassed by formula I. | Cl–CH$_2$–C(=CH$_2$)–O–C$_8$H$_{17}$ |
| (3-chloroprop-1-en-2-yloxy)decane and isomers encompassed by formula I. | Cl–CH$_2$–C(=CH$_2$)–O–C$_{10}$H$_{21}$ |
| (3-chloroprop-1-en-2-yloxy)dodecane and isomers encompassed by formula I. | Cl–CH$_2$–C(=CH$_2$)–O–C$_{12}$H$_{25}$ |
| (3-chloroprop-1-en-2-yloxy)tetradecane and isomers encompassed by formula I. | Cl–CH$_2$–C(=CH$_2$)–O–C$_{14}$H$_{29}$ |
| N,N-diethyl-2-(hexanyloxy)prop-2-en-1-amine and isomers encompassed by formula I. | (Et)$_2$N–CH$_2$–C(=CH$_2$)–O–C$_6$H$_{13}$ |
| N-(2-(hexanyloxy)allyl)-N,N-dimethylbutan-1-aminium chloride and isomers encompassed by formula I. | C$_4$H$_9$–N$^+$(Me)$_2$–CH$_2$–C(=CH$_2$)–O–C$_6$H$_{13}$, Cl$^-$ |
| 2-(hexanyloxy)-N,N-dimethylprop-2-en-1-amine and isomers encompassed by formula I. | Me$_2$N–CH$_2$–C(=CH$_2$)–O–C$_6$H$_{13}$ |
| 2-(hexanyloxy)-N,N-dimethylprop-2-en-1-amine and isomers encompassed by formula I. | Me$_2$N–CH$_2$–C(=CH$_2$)–O–C$_6$H$_{13}$ |
| 2-(hexanyloxy)-N,N,N-trimethylprop-2-en-1-aminium chloride and isomers encompassed by formula I. | Me$_3$N$^+$–CH$_2$–C(=CH$_2$)–O–C$_6$H$_{13}$, Cl$^-$ |

TABLE 1-continued

| Name | Structure |
|---|---|
| 2-(3-chloroprop-1-en-2-yloxy)butane and isomers encompassed by formula I. | Cl–CH$_2$–C(=CH$_2$)–O–C$_4$H$_9$ |
| 2-(3-chloroprop-1-en-2-yloxy)hexadecane and isomers encompassed by formula I. | Cl–CH$_2$–C(=CH$_2$)–O–C$_{16}$H$_{33}$ |
| 2-(3-chloroprop-1-en-2-yloxy)octadecane and isomers encompassed by formula I. | Cl–CH$_2$–C(=CH$_2$)–O–C$_{18}$H$_{37}$ |
| 2-(dodecan-2-yloxy)-N,N,N-triethylprop-2-en-1-aminium chloride and isomers encompassed by formula I. | (Et)$_3$N$^+$–CH$_2$–C(=CH$_2$)–O–C$_{12}$H$_{25}$  Cl$^-$ |
| 4-(2-(dodecan-2-yloxy)allyl)-morpholine and isomers encompassed by formula I. | morpholine-N–CH$_2$–C(=CH$_2$)–O–C$_{12}$H$_{25}$ |
| 2-(2-(dodecan-2-yloxy)-allylamino)ethanol and isomers encompassed by formula I. | HO–CH$_2$CH$_2$–NH–CH$_2$–C(=CH$_2$)–O–C$_{12}$H$_{25}$ |
| N-(2-(dodecan-2-yloxy)allyl)-butan-1-amine and isomers encompassed by formula I. | C$_4$H$_9$–NH–CH$_2$–C(=CH$_2$)–O–C$_{12}$H$_{25}$ |
| 2-(3-ethoxyprop-1-en-2-yloxy)dodecane and isomers encompassed by formula I. | EtO–CH$_2$–C(=CH$_2$)–O–C$_{12}$H$_{25}$ |
| triethyleneglycol methyl 2-hexyloxyallyl ether and isomers encompassed by formula I. | H$_3$C–(OH$_2$CH$_2$C)$_3$–O–CH$_2$–C(=CH$_2$)–O–C$_6$H$_{13}$ |
| polyethyleneglycol methyl 2-dodecyloxyallyl ether and isomers encompassed by formula I. | CH$_3$O–(CH$_2$CH$_2$O)$_n$–CH$_2$–C(=CH$_2$)–O–C$_{12}$H$_{25}$ |

In addition to substitution at the 2-position of the alkyl chain formed by $R_1$, $R_2$ and the carbon to $R_1$ and $R_2$ are attached, as depicted in Table 1, also preferred are structures wherein substitution is at any of the other secondary carbons of the alkyl chain. Further preferred are isomeric mixtures of such compounds.

As discussed above, the processes for preparing the compounds of the invention may result in the formation of mixtures of compounds of formula I, which can optionally be used directly in further applications and formulations, without the need for separation into individual compounds.

In another aspect, the invention provides a process for making the vinyl ethers of formula I. The process comprises:
providing an ether compound of formula A:

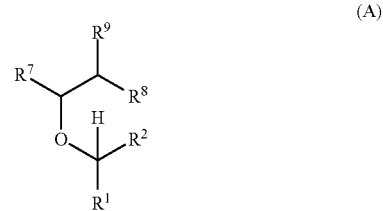

(A)

wherein R¹ and R² are as defined above; and
R⁷ is H or CH₂X, R⁸ is X, and R⁹ is H or CH₂X, wherein one of R⁷ or R⁹ is H; and
X is a halo group (F, Cl, Br, or I, preferably Cl); and
effecting an elimination reaction on the ether compound of formula A to form a vinyl containing compound;
and optionally substituting the vinyl containing compound with a nucleophile.

The ether compound of formula A may be prepared as described in applicants' copending U.S. patent application Ser. No. 12/430,171, filed Apr. 27, 2009 which is incorporated herein by reference in its entirety. Generally, the synthesis comprises the reaction of an alcohol compound with an olefin in the presence of an acidic etherification catalyst. Typically, an equimolar or slight excess of the olefin is used. A solvent may be used, although not required. The reaction may be conducted at elevated temperature, such as about 50 to 150° C. Once the desired amount of the ether compound product is formed (as determined, for instance, by gas chromatography), the reaction mixture is cooled and subjected to conventional workup. For instance, for removal of a homogeneous acid catalyst, the cooled mixture is added to water containing bicarbonate and/or chloride salts, and the organic liquid layer of the mixture containing the ether compound removed. The ether compound may be further purified by known techniques, such as distillation.

The alcohol of the above-described synthesis generally has the following formula:

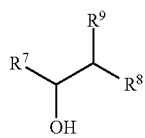

wherein R⁷, R⁸, and R⁹ are as defined above.

Preferred alcohols for the synthesis include: 1,3-dihalo-2-propanol and 2,3-dihalopropanol, or a mixture thereof. Particularly preferred are 1,3-dichloro-2-propanol and 2,3-dichloropropanol, or a mixture thereof.

The olefin for use in the above synthesis is preferably a linear or branched alpha-olefins (i.e., 1-alkenes) containing 4 to 22 carbon atoms, or a mixture of isomers of linear or branched 1-alkenes containing 4 to 22 carbon atoms together with their internal and/or tertiary olefin isomers. Preferably, the alkenes are linear and contain 6 to 18 carbon atoms. Non-limiting examples of particularly preferred alpha olefins include: 1-butene, 1-pentene, 1-hexene, 4-methyl-1-pentene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, or mixtures of two or more thereof.

As the olefin may be isomerized when contacted with the acidic etherification catalyst, it is not necessary to use an alpha-olefin, and internal olefins containing 4 to 22 carbon atoms, or mixtures of isomers of linear or branched alkenes are also suitable for use. Non-limiting examples of suitable internal olefins include: 2-butene, 2-pentene, 2-hexene, 3-hexene, 2-heptene, 3-heptene, 2-octene, 3-octene, 4-octene, 2-nonene, 3-nonene, 4-nonene, 2-decene, 3-decene, 4-decene, 5-decene, etc, or mixtures of two or more thereof.

Acidic etherification catalysts suitable for use in the synthesis of the ether compound include, but are not limited to, acidic ionic exchange resins, such as DOWEX™ DR-2030 available from The Dow Chemical Company, clays, zeolites, sulfonated polystyrene beads, and acids immobilized on a heterogeneous surface, such as tetrafluoroethanesulfonic acid on silica beads, Bronsted acids such as triflic (trifluoromethanesulfonic) acid, methanesulfonic acid, or sulfuric acid, Lewis acids such as BF₃ and its derivatives (e.g., dihydrate or ether), and trimethylsilyl triflate. The ratio of catalyst to reactants is not critical and is generally adjusted so as to obtain a desired reaction rate. Preferably, the catalyst is at a temperature of between about 50 and 150° C. during the process in order to facilitate the etherification reaction.

The elimination step of the process is typically conducted under basic conditions and results in the formation of a vinyl containing compound (corresponding to compounds of formula I wherein R³ is halo). Various bases may be used for the reaction, examples of which include, but are not limited to, sodium hydroxide, potassium hydroxide, sodium hydride, and alkoxides, such as potassium t-butoxide.

The vinyl containing compound is optionally reacted with a nucleophile to form additional compounds of formula I. Examples of suitable nucleophiles include, for instance, mono-alcohols (e.g., 2-phenoxyethanol, allyl alcohol, dimethyl-aminoethanol, cyclohexanol), alkylene glycol monoalkyl ethers (e.g., triethylene glycol monomethyl ether, methoxypolyethylene glycol), sodium sulfite, alkylamines (e.g., diethylamine, dimethylbutylamine, trimethylamine), alkyl- or arylphosphines (e.g. triethylphosphine, tributylphosphine, diphenylphosphine, diphenylphosphine-borane, triphenylphosphine).

The elimination and optional substitution steps of the process can be carried out in one-pot reaction. Such one-pot reaction is highly advantageous because it provides a resource-efficient manner in which compounds of formula I may be prepared. Typically, the ether compound, the base and optional nucleophile are reacted at elevated temperature, although this is not required. In addition, a solvent may optionally be used. Following sufficient time for the reaction to occur (e.g., 1 to 24 hours), the reaction mixture is cooled to ambient conditions, and then subjected to conventional workup. The formula I compound may optionally be further purified. Purification may be conducted using conventional techniques, such as distillation, extraction, filtration, chromatography, and/or crystallization.

The vinyl ether compounds of formula I contain a vinyl group (as well as other functional groups). The compounds, therefore, are capable of undergoing various downstream reactions, including, for instance, oligomerization or polymerization via the vinyl functionality. The formula I compounds also contain hydrophobic/hydrophilic character. As a consequence of this combination of functionalities, the formula I compounds have a wide variety of properties, allowing them to be used, for instance, as surfactants, polymerizable surfactants, as co-monomers for UV cure applications, as reactive diluents, and as co-monomers for high $T_g$/low $\epsilon_r$ polymers. The compounds, therefore, can be used in a broad spectrum of formulations and applications. By way of non-limiting example, the compounds may be used in: coating formulations, agricultural formulations, personal care formulations, oil and gas formulations, adhesive formulations, latex formulations, radiation curable formulations, and printing ink formulations.

The amount and composition of the compound of formula I to be used in any particular formulation varies depending on the application and the desired result and can be determined by a person of ordinary skill in the art without undue experimentation. For instance, if the compound of formula I is used as a surfactant, a typical usage concentration is at least about 0.01 weight percent of the compound, based on the total weight of the formulation.

As used in this specification, "alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl. "Alkenyloxy" means an alkenyl further consisting of a carbon-oxygen single bond, for example, allyloxy, butenyloxy, pentenyloxy, hexenyloxy, heptenyloxy, octenyloxy, nonenyloxy, and decenyloxy. "Alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, decoxy. "Poly(alkoxy)" means a polymeric or oligomeric substituent with one or more alkoxy groups as repeat unit(s), such as poly(ethylene glycol), poly (propylene glycol). "Alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl. "Alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl. "Alkynyloxy" means an alkynyl further consisting of a carbon-oxygen single bond, for example, pentynyloxy, hexynyloxy, heptynyloxy, octynyloxy, nonynyloxy, and decynyloxy. "Amine," in addition to —$NH_2$, also encompasses alkyl, alkenyl, alkoxy, alkenyloxy, or aryl, further consisting of at least one hydrogen-nitrogen or one carbon-nitrogen single bond(s), for example, amino, monomethylamino, dimethylamino, diethylamino "Ammonium" means an alkyl, alkenyl, alkoxy, alkenyloxy, or aryl, further consisting of at least one hydrogen-nitrogen or one carbon-nitrogen single bond(s) with the nitrogen atom bearing a positive charge (with e.g., halo as the counterion), for example, trimethylammonio, dimethylpropylammonio. "Aryl" means a cyclic, aromatic substituent consisting of hydrogen and carbon, for example, phenyl, methoxyphenyl, naphthyl, and biphenylyl. "Aryloxy" means an aryl further consisting of a carbon-oxygen single bond, for example, phenoxy, (methoxyphenyl)oxy. "Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, cycloheptenyl, cyclooctenyl, cyclodecenyl, norbornenyl, bicyclo[2.2.2]octenyl, tetrahydronaphthyl, hexahydronaphthyl, and octahydronaphthyl. "Cycloalkenyloxy" means a cycloalkenyl further consisting of a carbon-oxygen single bond, for example, cyclobutenyloxy, cyclopentenyloxy, cyclohexenyloxy, cycloheptenyloxy, cyclooctenyloxy, cyclodecenyloxy, norbornenyloxy, and bicyclo[2.2.2]octenyloxy. "Cycloalkyl" means a monocyclic or polycyclic, saturated substituent consisting of carbon and hydrogen, for example, cyclopropyl, cyclobutyl, cyclopentyl, cyclohexyl, cycloheptyl, cyclooctyl, cyclodecyl, norbornyl, bicyclo[2.2.2]octyl, and decahydronaphthyl. "Cycloalkoxy" means a cycloalkyl further consisting of a carbon-oxygen single bond, for example, cyclopropyloxy, cyclobutyloxy, cyclopentyloxy, cyclohexyloxy, cycloheptyloxy, cyclooctyloxy, cyclodecyloxy, norbornyloxy, and bicyclo[2.2.2]octyloxy. "Heterocycloalkyl" means a non-aromatic 3-12 atom ring system containing at least one heteroatom selected from nitrogen, oxygen, and sulfur. The heterocycloalkyl ring may be optionally fused to or otherwise attached to other heterocycloalkyl rings and/or non-aromatic hydrocarbon rings. Preferred heterocycloalkyl groups have from 3 to 7 members. A non-limiting example of a heterocycloalkyl group is morpholino. "Halo" means fluoro, chloro, bromo, and iodo. "Haloalkyl" means an alkyl further consisting of, from one to the maximum possible number of, identical or different, halos, for example, fluoromethyl, difluoromethyl, trifluoromethyl, 1-fluoromethyl, 2-fluoroethyl, 2,2,2-trifluoroethyl, chloromethyl, trichloromethyl, and 1,1,2,2-tetrafluoroethyl. "Phosphine" means an alkyl, alkenyl, alkoxy, alkenyloxy, or aryl, further consisting of at least one hydrogen-phosphor or one carbon-phosphor single bond(s), for example, phosphino, dimethylphosphino, diethylphosphino. "Phosphonium" means an alkyl, alkenyl, alkoxy, alkenyloxy, or aryl, further consisting of at least one hydrogen-phosphor or one carbon-phosphor single bond(s) with the phosphor atom bearing a positive charge, for example, trimethylphosphonio, dimethylpropylphosphonio.

The following examples are illustrative of the invention but are not intended to limit its scope. Unless otherwise indicated, the ratios, percentages, parts, and the like used herein are by weight.

EXAMPLES

Example A

Etherification of Alpha-Olefin with 1,3-Dichloro-2-Propanol

Exemplary ether compounds, precursors to the compounds of formula I, may be prepared by the following protocol. A bottom-drain Dean-Stark trap with a glass wool plug to retain the resin beads is charged with 16.2 g of DOWEX™ DR-2030 resin, the resin is wetted with 11.5 g of 1,3-dichloro-2-propanol, and the apparatus attached to a 1-L round bottom flask. The flask is charged with 1.1 mol of an alpha-olefin and 139.7 g of 1,3-dichloro-2-propanol (total of 1.17 mol). Vacuum is applied, and the 1-L flask heated such that distillate from the 1-L flask is condensed into the Dean Start trap containing the warmed resin, and returned to the 1-L flask. The temperature in the 1-L flask climbs with continued distillation. The reaction mixture is purified by distillation to afford alkyl 1,3-dichloropropyl ether.

Example B

Etherification of 1-Dodecene with 1,3-Dichloro-2-Propanol

An ether made substantially according to the protocol described in Example A is produced as follows. A 2-L reactive distillation apparatus is constructed as described here. A 2-L round-bottom flask with a magnetic stirrer is fitted into a heating mantle and connected to a distillate receiver. Distillate is condensed into the side arm distillate receiver containing a magnetic stirrer and temperature probe. A valved line between the distillate receiver and the 2-L flask gives a nominal volume of about 100 mL in the distillate receiver. Liquid is pumped from the bottom of the distillate receiver to a 21 inches long and ¾ inches in diameter stainless steel tube fitted on each end with 90 μm screen filters to provide a catalyst bed. A jacket system covering the catalyst containing pipe is heated using a recirculating hot oil bath. The outlet of the catalyst bed returns liquid to the distillate receiver. The system is connected to a vacuum pump such that the reactive distillation can be carried out at pressures of 10 to 300 torr. The catalyst bed of the 2-L reactive distillation apparatus is charged with 60 g of DOWEX™ DR-2030. The 2-L vessel is charged with 684.72 g (5.304 mol) of 1,3-dichloro-2-propanol and 843.05 g (5.009 mol) of 1-dodecene. The vacuum is adjusted to 22 torr, and the 2-L vessel heated to afford distillation at an initial temperature of 79° C., with a vapor temperature of 70° C. The catalyst bed oil bath is set to 110° C. to give a temperature in reaction product exiting the catalyst bed of 80-88° C. The condenser temperature is about −11° C. to −5° C. The distillate receiver temperature is 63 to 69° C. With additional heating, the bottoms temperature reaches 192° C. and the overhead temperature is 80° C. The mixture is cooled and unloaded. The solution in the distillate receiver and catalyst bed (96.30 g, 6.3% of mass loaded) is discarded. The solution in the 2-L vessel (1302.33 g, 85.2% of mass loaded) is analyzed by GC analysis (1.803 area %, 1.10 wt % of dodecene, 0.708 area %, 0.48 wt % of dodecanol, 0.01 area %, 0.03 wt % of 1,3-dichloro-2-propanol, 89.843 area %, 88.71 wt % of the C12 1,3-dichloropropyl ether). A portion (1298.01) is loaded to a 2-L round-bottom flask and purified by distillation at 0.2 to 0.6 torr using a 14" vacuum-jacketed Vigreux column topped with a reflux splitter. The first fraction (30.36 g) is collected using a 15:1 reflux ratio at an overhead temperature of 25 to 105° C. with a bottoms temperature of 146-189° C. The product fraction is collected using a 15:1 reflux ratio at an overhead temperature of 104 to 118° C. with a bottoms temperature of 190-220° C. to afford 1217.88 g (4.09 mol) of the 1,3-dichloropropyl ether of dodecane (1,3-dichloropropan-2-lyoxydodecane, 94.8 area % by GC analysis, mixture of positional isomers, 93.8% distilled yield). A 42.10-g residue remains as the distillation bottoms.

Example 1

Triethyleneglycol methyl 2-dodecyloxyallyl ether

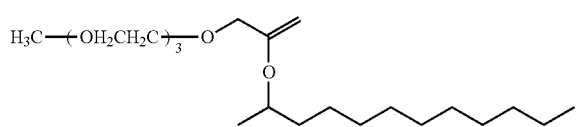

Into a 250 ml 3-neck round-bottomed flask equipped with overhead stirrer, condenser, and additional funnel is added 41.5 g of triethylene glycol monomethyl ether and then purged with flow nitrogen at room temperature for 15 minutes. 10 g of NaOH (beads) is added at room temperature. The mixture is heated under vacuum using an oil bath to 120° C. for 1.5 h. After that, 20 g (1,3-dichloropropan-2-yloxy)dodecanes is added through the additional funnel under nitrogen over about 40 minutes and stirred for 1.5 h at 120° C. The oil bath temperature is then lowered to 80-90° C. and 10 ml of water added. The reaction mixture is stirred at this temperature for another 20 minutes. The reaction mixture is transferred to a separation funnel and diluted with 100 ml of water. The mixture is extracted with ethyl acetate (3×100 ml). GC analysis of the reaction mixture shows no remaining starting material, and a single new group of peaks that are determined to be target product by further GC/MS analysis. The combined organic phases are washed with water (100 ml×3). The solvents are removed on a rotary evaporator and the product is dried in a vacuum oven at 50° C. overnight to afford 23.5 of yellow oil as the final product. Yield: 90%. GC-MS (EI+): Mass calculated for $C_{22}H_{44}O_5$ ($M^+$): 388.3. Found 388.3 (100%), multiple isomers.

Example 2

2-(3-(2-phenoxyethoxy)prop-1-en-2-yloxy)bicyclo[2.2.1]heptane

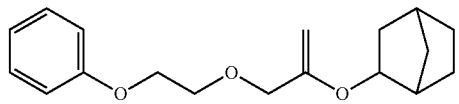 [SMILES: C=C(COCCOc1ccccc1)OC1CC2CCC1C2]

A steel reactor, equipped with overhead stirrer, condenser, nitrogen inlet, and temperature probe, is purged with nitrogen for about 5 min and charged with (1,3-dichloropropan-2-yloxy)bicyclo[2.2.1]heptane (150 mmol, 33.3 g, 1.0 eq), 2-phenoxyethanol (165 mmol, 22.8 g, 1.1 eq), and NaOH (330 mmol, 13.2 g, 2.2 eq). The reaction mixture is heated to 100° C. and stirred. GC samples are taken in regular intervals. After about 7 h, NaOH (150 mmol, 6.0 g, 1 eq) is added and stirred for additional 15 h at 100° C. The cooled reaction mixture is then transferred into a separation funnel. Water (200 mL) and ethyl acetate (200 mL) are added, the mixture is shaken and the organic phase collected. The water phase is extracted twice with 150 mL aliquots of ethyl acetate. The combined organic phases are washed with saturated ammonium chloride solution and brine (100 mL aliquots), until a neutral pH is obtained. The organic phase is dried over sodium sulfate, filtered and the solvent removed under reduced pressure. The compound is distilled under vacuum on a Kugelrohr to collect two fractions. Care is taken to minimize the heat history during distillation as both isomerization and polymerization can occur, which reduces the reaction yield significantly. The $1^{st}$ fraction is collected at 155° C. and contains unreacted starting material. The $2^{nd}$ fraction is collected at 175° C. and contains the pure product as a viscous, colorless oil (10.8 g 34.7 mmol, 23%). MS (EI+) Mass calc'd for $C_{18}H_{24}O_3$ ($M^+$): 288.17. found 288.2.

Example 3

(3-(Allyloxy)prop-1-en-2-yloxy)hexanes

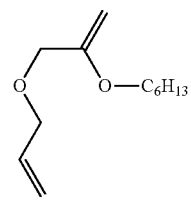

In a 35 mL microwave tube, equipped with septum, stirbar, and under $N_2$ atmosphere, sodium hydride (60% suspension in mineral oil, 22.0 mmol, 880 mg, 2.2 eq) is suspended in dry 1,4-dioxane (10 mL) under nitrogen. While stirring, allyl alcohol (20.0 mmol, 1.16 g, 2.0 eq) is added dropwise via syringe at room temperature. The mixture is stirred until hydrogen development has ceased and dichloropropan-2-yloxy)hexanes (10.0 mmol, 2.13 g, 1.0 eq) is added. The reaction is heated in the microwave to 100° C. for 1 h. Solvent and product mixture are separated by fractionated distillation under vacuum. 1.68 g of distillate is obtained which contains the desired product at 61% (GC-MS) purity. The composition of the distillate is as follows (GC-MS): (3-(allyloxy)prop-1-en-2-yloxy)hexanes (≥3 isomers): GC-MS (EI$^+$): mass calc'd for $C_{12}H_{22}O_2$ (M$^+$): 198.16. found 198.2 (~61%). (3-chloroprop-1-en-2-yloxy)hexanes (≥4 isomers): GC-MS (EI$^+$): mass calc'd for $C_9H_{17}ClO$ (M$^+$): 176.09. found 176.1 (~11%). (1,3-dichloropropan-2-yloxy)hexanes (≥2 isomers): GC-MS (EI$^+$): mass calc'd for $C_9H_{18}Cl_2O$ (M$^+$): 234.14. found 212.1 (~24%). (1-(allyloxy)-3-chloropropan-2-yloxy)hexanes (≥2 isomers): GC-MS (EI$^+$): mass calc'd for $C_{12}H_{23}ClO_2$ (M$^+$): 234.14. found 234.1 (~1%).

Example 4

(3-Chloroprop-1-en-2-yloxy)hexanes

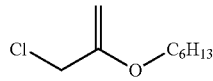

Base Addition Method. A 500-mL round-bottom flask equipped with a magnetic stir bar, nitrogen bubbler, and addition funnel is charged with 21.20 g (0.099 mol) of 1,3-dichloropropan-2-yloxyhexanes and 25 g of THF. To the solution is added dropwise 14.39 g (0.128 mol) of potassium tert-butoxide in 30.85 g of THF. The temperature increases from 23 to 37° C. during the addition. After stirring overnight at ambient temperature, the solution is diluted with 50 mL of ethyl acetate and 40 mL of water. The pH is decreased from 13.5 to 7.8 by the dropwise addition of 37% hydrochloric acid. The organic phase is separated, dried (magnesium sulfate), filtered, and evaporated to a residue of 17.09 g, GC analysis of the residual oil finds 85 area % of 3-chloroprop-1-en-2-yloxyhexanes (0.082 mol, 83% yield corrected for 85% purity) and 4.4 area % of 1,3-dichloropropan-2-yloxyhexanes. $^1$H-NMR (CHCl$_3$, 300 MHz): δ=0.88-0.98 (m (unresolved overlaid triplets of two isomers), 6H, CH$_3$), 1.1-1.6 (m, two isomers, CH$_2$), 3.9 (d, 2H, Cl—CH$_2$), 4.0-4.1 (m, 2H, C=CH$_2$ and O—CH), 4.2 (d, 1H, C=CH$_2$). $^{13}$C-NMR (CHCl$_3$, 75 MHz): 7.3, 11.9, 16.5, 20.5, 24.0, 25.2, 33.2, 33.9 (C$_6$, two isomers), 43.5 (Cl—CH$_2$, two isomers), 71.2 (CH$_3$—C(O)H—CH$_2$), 76.0 (CH$_2$—C(O)H—CH$_2$), 83.1, 83.3 (C=CH$_2$, two isomers), 154.8 and 155.2 (O—C=CH$_2$, two isomers).

Addition to Base Method. A 1-L round-bottom flask equipped with an overhead stirrer, addition funnel, nitrogen bubbler and temperature probe is charged with 43.91 g (0.39 mol) of potassium t-butoxide and 100 mL of THF. The mixture is chilled in an ice bath, and 41.7 g (0.196 mol) of 1,3-dichloropropan-2-yloxyhexanes is added dropwise with stirring, followed by an additional 50 mL of THF. The maximum temperature reached is 25° C. After stirring overnight at ambient temperature, the slurry is diluted with 100 mL of ethyl acetate and 100 mL of water. The pH is adjusted to 7 by addition of drops of 37% hydrochloric acid. The lower aqueous phase is removed, and the upper organic phase treated with anhydrous magnesium sulfate, filtered, and evaporated to a residue of 34.52 g. The residual oil is distilled, and the fraction boiling at 46° C., 2 to 3 torr, is collected to afford 30.71 g (0.174 mol, 89% yield) of 3-chloroprop-1-en-2-yloxyhexanes.

Example 5

Polyethyleneglycol methyl 2-dodecyloxyallyl ether

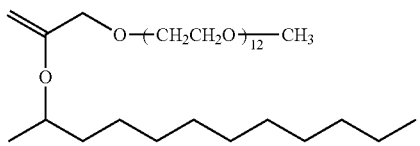

Using methoxypolyethylene glycol (available as CARBOWAX™ MPEG 550 from The Dow Chemical Company), NaOH, and (1,3-dichloropropan-2-yloxy)dodecanes as starting materials, and following the general procedure of Example 1 while making non-critical variations, the title compound is obtained.

Example 6

2-(3-(Allyloxy)prop-1-en-2-yloxy)bicyclo[2.2.1]heptanes

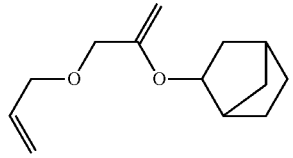

Using 2-(1,3-dichloropropan-2-yloxy)bicyclo[2.2.1]heptane, NaH, and allyl alcohol as starting materials, and following the general procedure of Example 3 while making non-critical variations, the title compound is obtained. GC-MS (EI$^+$): mass calc'd for $C_{13}H_{20}O_2$ (M$^+$): 208.15. found 208.2 (62.5%).

Example 7

(3-(Allyloxy)prop-1-en-2-yloxy)dodecanes

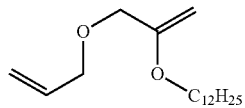

Using (1,3-dichloropropan-2-yloxy)dodecanes, sodium hydride, and allyl alcohol as starting materials, and following the general procedure of Example 3 while making non-critical variations, the title compound is obtained (≥5 isomers). GC-MS (EI$^+$): mass calc'd for $C_{18}H_{34}O_2$ (M$^+$): 282.26. found 282.2 (~61%).

Example 8

2-(2-(Hexanyloxy)allyloxy)-N,N-dimethylethanamines

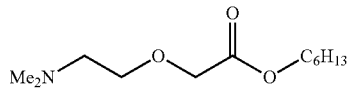

Using (1,3-dichloropropan-2-yloxy)hexanes, sodium hydride, and dimethylaminoethanol as starting materials, and following the general procedure of Example 3 while making non-critical variations, the title compound is obtained. $^1$H-NMR (CHCl$_3$, 300 MHz): δ=0.82-0.95 (m, 3H, CH$_3$), 1.15-1.72 (m, 9H, CH$_3$, CH$_2$), 2.27 (s, 6H, N(CH$_3$)$_2$), 2.52 (t, $^3$J=5.9 Hz, 2H, Me$_2$NCH$_2$), 3.56 (t, $^3$J=5.9 Hz, 2H, Me$_2$NCH$_2$CH$_2$O), 3.51-3.69 (m, 1H, O—CHR$_2$), 3.83-3.92 (m, 2H, OCH$_2$), 3.99-4.03 (m, 1H, R$_2$C=CH$_2$), 4.14-4.19 (m, 1H, R$_2$C=CH$_2$). GC-MS (EI$^+$): mass calc'd for C$_{13}$H$_{27}$NO$_2$ (M$^+$): 229.20. found 229.2 (~96%, 2-(2-(hexanyloxy)allyloxy)-N,N-dimethylethanamines, ≥2 isomers).

Example 9

Mixtures of 2-(2-(dodecanyloxy)allyloxy)-N,N-dimethylethanamine isomers/N,N-dimethyl-2-(2-methyldodecanyloxy)prop-2-en-1-amine isomers

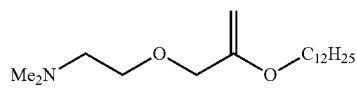

Using (1,3-dichloropropan-2-yloxy)dodecanes, sodium hydride, and dimethylaminoethanol as starting materials, and following the general procedure of Example 3 while making non-critical variations, the title compounds are obtained. GC-MS and QTOF ES$^+$. QTOF ES$^+$: mass calc'd for C$_{19}$H$_{39}$NO$_2$H (M+H$^+$): 314.31. found 314.307 (78.7%, 2-(2-(dodecanyloxy)allyloxy)-N,N-dimethylethanamines, isomers), mass calc'd for C$_{17}$H$_{35}$NOH (M+H$^+$): 270.28. found 270.27 (21.3%, N,N-dimethyl-2-(2-methyldodecanyloxy)prop-2-en-1-amines, ≥5 isomers).

Example 10

Mixtures of 2-(2-(dodecanyloxy)allyloxy)-N,N,N-trimethylethanaminium bromide isomers/2-(dodecanyloxy)-N,N,N-trimethylprop-2-en-1-aminium bromide isomers

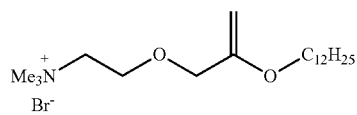

A steel pressure tube is filled with a mixture of 2-(2-(dodecanyloxy)allyloxy)-N,N-dimethylethanamine isomers and N,N-dimethyl-2-(2-methyldodecanyloxy)prop-2-en-1-amine isomers from Example 9 (4 g, 12.8-14.8 mmol, ~1.0 eq) and cooled to −78° C. The tube is evacuated and then filled with methyl bromide (2.0 M in tert-butyl methyl ether, 28-32 g, 64-74 mmol, ~5.0 eq) and sealed. The tube is shaken at room temperature for 2-3 d. After the reaction is complete, the tube was again cooled to −78° C., and the contents transferred to a round bottom flask while cold. Excess methyl bromide and the solvent are removed under reduced pressure. Water, and traces of starting material may be removed by re-dissolving the residue in a minimal amount of diethyl ether/ethyl acetate (1:1) and subsequent precipitation from pentanes or heptanes. The quaternary salts are obtained as off-white compounds in quantitative yield. HRMS (Q-TOF ES$^+$): mass calc'd for C$_{20}$H$_{42}$NO$_2$ (M$^+$): 328.321. found 328.324 2-(2-(dodecanyloxy)allyloxy)-N,N,N-trimethylethanaminium ions, mass calc'd for C$_{18}$H$_{38}$NO (M$^+$): 284.295. found 284.292 2-(dodecanyloxy)-N,N,N-trimethylprop-2-en-1-aminium ions.

Example 11

(3-Chloroprop-1-en-2-yloxy)bicyclo[2.2.1]heptanes

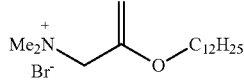

Using (1,3-dichloropropan-2-yloxy)bicyclo[2.2.1]heptanes and potassium tert-butoxide as starting materials, and following the general procedure of Example 4 while making non-critical variations, the title compound is obtained. MS (EI$^+$) Mass calc'd for C$_{10}$H$_{15}$ClO (M$^+$): 186.08. found 186.1.

Example 12

Sodium 2-(hexyloxy)prop-2-ene-1-sulfonate

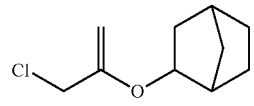

A 50-mL round-bottom flask equipped with a magnetic stir bar, nitrogen bubbler, and reflux condenser is charged with 1.03 g (5.8 mmol) of 3-chloroprop-1-en-2-yloxyhexanes, 1.05 g (83 mmol) of sodium sulfite, 0.07 g of sodium carbonate, and 20.4 g of water. The mixture is heated to reflux for 4 hours, then cooled to ambient temperature. The cooled solution is extracted with 10 mL of ethyl acetate. The separated aqueous phase is concentrated by rotary evaporation to afford 10.75 g of a clear solution. HPLC analysis with evaporative light scattering detection gives a single peak. $^{13}$C-NMR (H$_2$O, 75 MHz): 11.7, 16.2, 20.8, 21.1, 24.8, 28.2, 29.8, 37.2, 37.6 (C$_6$, two isomers), 59.7 and 65.4 (NaSO$_3$—CH$_2$, two isomers), 76.6 (CH$_3$—C(O)H—CH$_2$), 81.3 (CH$_2$—C(O)H—CH$_2$), 90.7, 91.1 (C=CH$_2$, two isomers), 155.3 and 155.8 (O—C=CH$_2$, two isomers).

Example 13

(3-Chloroprop-1-en-2-yloxy)octanes

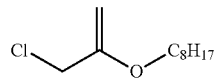

Using 1,3-dichloropropan-2-yloxyoctanes and potassium tert-butoxide as starting materials, and following the general procedure of Example 4 while making non-critical variations, the title compound is obtained (b.p. 75° C. at 1.5 torr). $^1$H-NMR (CHCl$_3$, 300 MHz): δ=0.88-0.98 (m (unresolved overlaid triplets of isomers), CH$_3$), 1.1-1.8 (m, isomers, CH$_2$), 3.9 (d, 2H, Cl—CH$_2$), 4.0-4.1 (m, 2H, C=CH$_2$ and O—CH), 4.3 (d, 1H, C=CH$_2$). $^{13}$C-NMR (CHCl$_3$, 75 MHz): multiple peaks 10-35 (C$_8$, isomers), 45.8 (Cl—CH$_2$, isomers), 73.3 (CH$_3$—C(O)H—CH$_2$), 78.4 (CH$_2$—C(O)H—CH$_2$), 85.3, 85.5 (C=CH$_2$, isomers), 156.8 and 157.2 (O—C=CH$_2$, isomers).

Example 14

(3-Chloroprop-1-en-2-yloxy)decanes

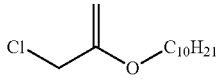

Using 1,3-dichloropropan-2-yloxydecanes and potassium tert-butoxide as starting materials, and following the general procedure of Example 4 while making non-critical variations, the title compound is obtained (b.p. 100° C. at 1.3 torr).

Example 15

(3-Chloroprop-1-en-2-yloxy)dodecanes

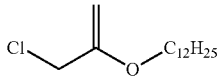

Using 1,3-dichloropropan-2-yloxydodecanes and potassium tert-butoxide as starting materials, and following the general procedure of Example 4 while making non-critical variations, the title compound is obtained (b.p. 110° C. at 1.3 torr).

Example 16

(3-Chloroprop-1-en-2-yloxy)tetradecanes

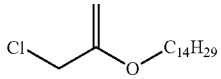

Using 1,3-dichloropropan-2-yloxytetradecanes and potassium tert-butoxide as starting materials, and following the general procedure of Example 4 while making non-critical variations, the title compound is obtained (b.p. 130° C. at 1.5 torr).

Example 17

N,N-Diethyl-2-(hexanyloxy)prop-2-en-1-amines

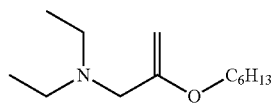

In a 35 mL microwave tube, equipped with septum, stirbar, and under N$_2$ atmosphere, potassium tert-butoxide (20.0 mmol, 2.24 g, 2.0 eq) is suspended in dry 1,4-dioxane (10 mL) under nitrogen and (1,3-dichloropropan-2-yloxy)hexanes (10.0 mmol, 2.13 g, 1.0 eq) is added. The reaction mixture solidifies and becomes slightly warm. 1,4-Dioxane (5 mL) is added to reduce the viscosity of the mixture, and diethylamine (15.0 mmol, 1.10 g, 1.5 eq) is added. The reaction mixture is heated for 2 min at 100° C. in the microwave to liquefy the mixture and thoroughly stirred. The mixture is then heated in the microwave to 100° C. for 1 h. The mixture is poured into saturated ammonium chloride solution, which is then extracted twice with ethyl acetate. The combined organic phases are extracted with saturated aqueous ammonium chloride and then brine, until a neutral pH is obtained. The organic phase is dried over sodium sulfate, filtered and the solvent removed under reduced pressure. A sample of the reaction mixture is analyzed by GC-MS and Q-TOF HRMS-MS/MS. GC-MS (EI$^+$): mass calc'd for C$_{13}$H$_{27}$NOH (M+H$^+$): 214.217. found 214.212 (~92%).

Example 18

Mixtures of N-(2-(hexanyloxy)allyl)-N,N-dimethylbutan-1-aminium chlorides/2-(hexanyloxy)-N,N-dimethylprop-2-en-1-amine isomers

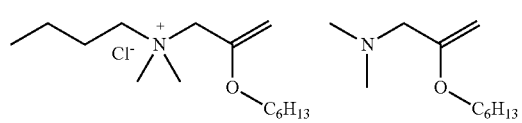

Using (1,3-dichloropropan-2-yloxy)hexanes, potassium tert-butoxide, and dimethylbutylamine as starting materials, and following the general procedure of Example 17 while making non-critical variations, the title compound is obtained. LC-MS (ES$^+$): mass calc'd for C$_{15}$H$_{32}$NO (M$^+$): 242.248. found 242.255 (~50.0%, N-(2-(hexanyloxy)allyl)-N,N-dimethylbutan-1-aminium, 3-4 isomers), mass calc'd for C$_{11}$H$_{23}$NOH (M+H$^+$): 186.186. found 186.192 (~27.1%), remaining peaks are other isomers.

Example 19

Mixtures of 2-(hexanyloxy)-N,N-dimethylprop-2-en-1-amine isomers/2-(hexanyloxy)-N,N,N-trimethylprop-2-en-1-aminium chlorides

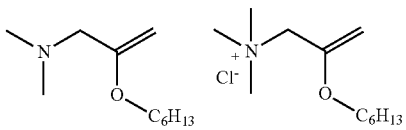

Using (1,3-dichloropropan-2-yloxy)hexanes, potassium tert-butoxide, and trimethylamine as starting materials, and following the general procedure of Example 17 while making non-critical variations, the title compound is obtained. LC-MS (ES$^+$): mass calc'd for $C_{11}H_{23}NOH$ (M+H$^+$): 186.186. found 186.193 (~80.6%, 2-(hexanyloxy)-N,N-dimethylprop-2-en-1-amine isomers), mass calc'd for $C_{12}H_{26}NO$ (M$^+$): 200.201. found 200.210 (~19.4%, 2-(hexanyloxy)-N,N,N-trimethylprop-2-en-1-aminium).

Examples 20-29

Additional Compounds of Formula I

Following the general procedures of the foregoing examples and making appropriate substitutions of starting materials, the compounds in Table 2 are prepared.

TABLE 2

| Ex. | Name | Structure | Analysis |
|---|---|---|---|
| 20 | 2-(3-chloroprop-1-en-2-yloxy)butane | Cl—CH$_2$—C(=CH$_2$)—O—C$_4$H$_9$ | b.p. 100° C. at 28 torr <br> $^{13}$C-NMR (CHCl$_3$, 75 MHz): 9.8 (CH$_3$CH$_2$), 19.9 (CH$_3$CH(O)), 28.8 (CH$_3$CH$_2$), 45.7 (Cl—CH$_2$), 74.5 (CH$_3$—C(O)H—CH$_2$), 85.5 (C=CH$_2$), 158.8 (O—C=CH$_2$) |
| 21 | 2-(3-chloroprop-1-en-2-yloxy)hexadecane | Cl—CH$_2$—C(=CH$_2$)—O—C$_{16}$H$_{33}$ | b.p. 140° C. at 0.5 torr <br> $^{13}$C-NMR (CHCl$_3$, 75 MHz): multiple peaks 10-35 (C$_{16}$, isomers), 45.8 (Cl—CH$_2$, isomers), 73.4 (CH$_3$—C(O)H—CH$_2$), 78.4 (CH$_2$—C(O)H—CH$_2$), 85.3, 85.5 (C=CH$_2$, isomers), 156.9 and 157.2 (O—C=CH$_2$, isomers). |
| 22 | 2-(3-chloroprop-1-en-2-yloxy)octadecane | Cl—CH$_2$—C(=CH$_2$)—O—C$_{18}$H$_{37}$ | b.p. 148° C. at 0.4 torr <br> $^{13}$C-NMR (CHCl$_3$, 75 MHz): multiple peaks 10-35 (C$_{18}$, isomers), 45.8 (Cl—CH$_2$, isomers), 73.4 (CH$_3$—C(O)H—CH$_2$), 78.4 (CH$_2$—C(O)H—CH$_2$), 85.3, 85.5 (C=CH$_2$, isomers), 156.8 and 157.2 (O—C=CH$_2$, isomers). |
| 23 | 2-(dodecan-2-yloxy)-N,N,N-triethylprop-2-en-1-aminium chloride | (Et)$_3$N$^+$—CH$_2$—C(=CH$_2$)—O—C$_{12}$H$_{25}$  Cl$^-$ | LC-MS (EI$^+$): $C_{21}H_{44}NO$, Exact Mass 326.342290 |
| 24 | 4-(2-(dodecan-2-yloxy)allyl)-morpholine | morpholine-N—CH$_2$—C(=CH$_2$)—O—C$_{12}$H$_{25}$ | $^{13}$C-NMR (CHCl$_3$, 75 MHz): multiple peaks 10-35 (C$_{12}$, isomers), 52.4 (N—CH$_2$ CH$_2$O), 61.8 (NCH$_2$C=C), 66.0 (N—CH$_2$ CH$_2$O), 72.3 (CH$_3$—C(O)H—CH$_2$), 78.4 (CH$_2$—C(O)H—CH$_2$), 83.2, 83.3 (C=CH$_2$, isomers), 156.3 and 156.7 (O—C=CH$_2$, isomers). |
| 25 | 2-(2-(dodecan-2-yloxy)-allylamino)ethanol | HO—CH$_2$CH$_2$—NH—CH$_2$—C(=CH$_2$)—O—C$_{12}$H$_{25}$ | $^{13}$C-NMR (CHCl$_3$, 75 MHz): multiple peaks 10-35 (C$_{12}$, isomers), 49.9 (N—CH$_2$ CH$_2$O), 52.8 (NCH$_2$C=C), 60.8 (N—CH$_2$ CH$_2$O), 72.5 (CH$_3$—C(O)H—CH$_2$), 78.5 (CH$_2$—C(O)H—CH$_2$), 82.5, 82.6 (C=CH$_2$, isomers), 158.5 and 158.8 (O—C=CH$_2$, isomers). |

TABLE 2-continued

| Ex. | Name | Structure | Analysis |
|---|---|---|---|
| 26 | N-(2-(dodecan-2-yloxy)allyl)-butan-1-amine | 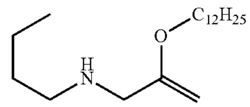 | $^{13}$C-NMR (CHCl$_3$, 75 MHz): multiple peaks 10-35 (C$_{12}$, isomers), 47.3 (N—CH$_2$ CH$_2$), 52.8 ( NCH$_2$C=C ), 72.5 (CH$_3$—C(O)H—CH$_2$), 78.5 (CH$_2$—C(O)H—CH$_2$), 81.5, 81.6 (C=CH$_2$, isomers), 158.3 and 158.8 (O—C=CH$_2$, isomers). |
| 27 | 2-(3-ethoxyprop-1-en-2-yloxy)dodecane | 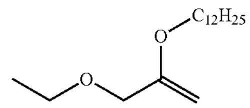 | $^{13}$C-NMR (CHCl$_3$, 75 MHz): multiple peaks 10-35 (C$_{12}$, isomers), 64.6 (O—CH$_2$ CH$_2$), 71.7 (OCH$_2$C=C), 72.5 (CH$_3$—C(O)H—CH$_2$), 78.5 (CH$_2$—C(O)H—CH$_2$), 81.7 81.8 (C=CH$_2$, isomers), 157.1 and 157.5 (O—C=CH$_2$, isomers). |
| 28 | triethyleneglycol methyl 2-hexyloxyallyl ether | 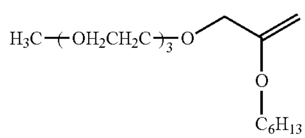 | $^{13}$C-NMR (CHCl$_3$, 75 MHz): multiple peaks 10-35 (C$_{12}$, isomers), 60.7 (O—CH$_3$), 70-75 (OCH$_2$ multiple peaks), 78.6 (CH$_2$—C(O)H—CH$_2$), 84.7, 84.8 (C=CH$_2$, isomers), 159.5 and 159.8 (O—C=CH$_2$, isomers). |
| 29 | polyethyleneglycol methyl 2-dodecyloxyallyl ether (n is about 8) | 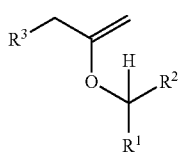 | $^{13}$C-NMR (CHCl$_3$, 75 MHz): multiple peaks 10-35 (C$_{12}$, isomers), 60.7 (O—CH$_3$), 70-75 (OCH$_2$ multiple peaks), 78.6 (CH$_2$—C(O)H—CH$_2$), 83.1, 83.2 (C=CH$_2$, isomers), 1578 and 158.2 (O—C=CH$_2$, isomers). |

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A compound of formula I:

(I)

wherein $R^1$ is C$_1$-C$_{12}$ alkyl;
$R^2$ is C$_1$-C$_{23}$ alkyl;
$R^3$ is SO$_3$$^-$M$^+$, a tertiary amine, a quaternary ammonium, a tertiary phosphine, a quaternary phosphonium, alkenyloxy, alkoxy, poly(alkoxy), alkynyloxy, aryloxy, cycloalkenyloxy, cycloalkoxy, halo, haloalkyloxy, aminoalkyloxy, (trialkylammonio)alkyloxy, hydroxyalkyl-amino, aryloxy-alkoxy, heterocycloalkyl, or thioether;
M$^+$ is H$^+$ or a monovalent or divalent cation, wherein the total number of carbon atoms in R$^1$, R$^2$ and the carbon to which they are attached is 4 to 22, and wherein the alkoxy group of R$^3$ is ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, or decoxy.

2. A compound according to claim 1 wherein R$^1$ is methyl.

3. A compound according to claim 1 wherein R$^2$ is a C$_1$-C$_{19}$ alkyl.

4. A compound according to claim 1 wherein R$^3$ is tertiary amine, a quaternary ammonium, alkenyloxy, alkoxy, poly(alkoxy), aryloxy, hydroxyalkyl-amino, aryloxy-alkoxy, heterocycloalkyl, or halo.

5. A compound according to claim 1 selected from the group consisting of: triethyleneglycol methyl 2-dodecyloxyallyl ether; (3-(allyloxy)prop-1-en-2-yloxy)hexane; (3-chloroprop-1-en-2-yloxy)hexane; polyethyleneglycol methyl 2-dodecyloxyallyl ether; (3-(allyloxy)prop-1-en-2-yloxy) dodecane; 2-(2-(hexanyloxy)allyloxy)-N,N-dimethylethanamine; 2-(2-(dodecanyloxy)allyloxy)-N,N-dimethylethanamine; N,N-dimethyl-2-(2-methyldodecanyloxy)prop-2-en-1-amine; 2-(2-(dodecanyloxy)allyloxy)-N,N,N-trimethylethanaminium bromide; 2-(dodecanyloxy)-N,N,N-trimethylprop-2-en-1-aminium bromide; sodium 2-(hexyloxy)prop-2-ene-1-sulfonate; (3-chloroprop-1-en-2-yloxy)octane; (3-chloroprop-1-en-2-yloxy)decane; (3-chloroprop-1-en-2-yloxy)dodecane; (3-chloroprop-1-en-2-yloxy)tetradecane; N,N-diethyl-2-(hexanyloxy)prop-2-en-1-amine; N-(2-(hexanyloxy)allyl)-N,N-dimethylbutan-1- aminium chloride; 2-(hexanyloxy)-N,N-dimethylprop-2-en-1-amine; 2-(hexanyloxy)-N,N-dimethylprop-2-en-1-amine; 2-(hexanyloxy)-N,N,N-trimethylprop-2-en-1-aminium chloride; 2-(3-chloroprop-1-en-2-yloxy)butane; 2-(3-chloroprop-1-en-2-yloxy)hexadecane; 2-(3-chloroprop-1-en-2-yloxy)octadecane; 2-(dodecan-2-yloxy)-N,N,N-triethylprop-2-en-1-aminium chloride; 4-(2-(dodecan-2-yloxy)allyl)-morpholine; 2-(2-(dodecan-2-yloxy)-allylamino)ethanol; N-(2-(dodecan-2-yloxy)allyl)-butan-1-amine; 2-(3-ethoxyprop-1-en-2-yloxy)dodecane; triethyleneglycol methyl 2-hexyloxyallyl ether; and polyethyleneglycol methyl 2-dodecyloxyallyl ether; or a structural isomers thereof.

6. A composition comprising two or more compounds according to claim 1.

7. A formulation selected from a coating formulation, an agricultural formulation, a personal care formulation, an oil and gas formulation, an adhesive formulation, a latex formulation, a radiation curable formulation, and a printing ink formulation, comprising a compound according to claim 1 or a mixture of two or more thereof.

8. A process for making the compound of claim 1, the process comprising:
providing an ether compound of formula A:

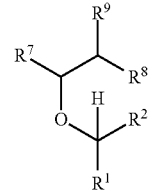

(A)

wherein $R^1$ and $R^2$ are as defined above; and
$R^7$ is H or $CH_2X$, $R^8$ is X, and $R^9$ is H or $CH_2X$, wherein one of $R^7$ or $R^9$ is H; and
X is a halo group; and
effecting an elimination reaction on the ether compound of formula A to form a vinyl containing compound;
and optionally substituting the vinyl containing compound with a nucleophile.

* * * * *